United States Patent
Superak

(10) Patent No.: US 7,166,772 B2
(45) Date of Patent: Jan. 23, 2007

(54) INBRED PUMPKIN LINE ZYPMB24

(75) Inventor: Theodore H. Superak, Davis, CA (US)

(73) Assignee: Harris Moran Seed Company, Modesto, CA (US)

( * ) Notice: Subject to any disclaimer, the term of this patent is extended or adjusted under 35 U.S.C. 154(b) by 0 days.

(21) Appl. No.: 11/005,528

(22) Filed: Dec. 6, 2004

(65) Prior Publication Data

US 2006/0123517 A1 Jun. 8, 2006

(51) Int. Cl.
- *A01H 5/00* (2006.01)
- *A01H 5/10* (2006.01)
- *A01H 4/00* (2006.01)
- *A01H 1/00* (2006.01)
- *C12N 15/82* (2006.01)

(52) U.S. Cl. .................. 800/310; 800/260; 800/278; 800/279; 800/295; 800/300; 800/301; 800/302; 800/303; 435/410

(58) Field of Classification Search .............. 800/260, 800/265, 266, 267, 274, 278, 300–302, 310
See application file for complete search history.

(56) References Cited

U.S. PATENT DOCUMENTS 5,523,520 A    6/1996    Hunsperger et al.

OTHER PUBLICATIONS

Eshed, et al., 1996. Less-than-additive epistatic interactions of quantitative trait loci in tomato. Genetics. 143:1807-1817.
Kraft, et al., 2000. Linkage disequilibrium and fingerprinting in sugar beet. Theor. Appl. Genet. 101:323-326.

*Primary Examiner*—David H. Kruse
*Assistant Examiner*—Keith O. Robinson
(74) *Attorney, Agent, or Firm*—Jondle & Associates P.C.

(57) ABSTRACT

An inbred pumpkin line, designated ZYPMB24, is disclosed. The invention relates to the seeds of inbred pumpkin line ZYPMB24, to the plants and plant parts of inbred pumpkin line ZYPMB24 and to methods for producing a pumpkin plant, either inbred or hybrid, by crossing the inbred line ZYPMB24 with itself or another pumpkin line. The invention further relates to methods for producing a pumpkin plant containing in its genetic material one or more transgenes and to the transgenic plants produced by that method and to methods for producing other inbred pumpkin lines derived from the inbred ZYPMB24.

41 Claims, No Drawings

INBRED PUMPKIN LINE ZYPMB24

BACKGROUND OF THE INVENTION

The present invention relates to a new and distinctive inbred pumpkin line, designated ZYPMB24. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as smoothness, color, shape and size, flesh color or texture, leaf shape and size, vine length and branching pattern, resistance to diseases and insects, tolerance to drought and heat, plant habit and size, easier harvest ability, less need for fertilizers, peduncle size and color, shell hardness and seed quality.

Practically speaking, all cultivated forms of ornamental or Halloween pumpkin belong to genus *Cucurbita* that is grown for its ornamental fruit. As a crop, pumpkins are grown commercially almost exclusively in the United States wherever environmental conditions permit the production of an economically viable yield. They are harvested by hand. Pumpkins usually develop a running vine on the soil, but many of today's pumpkins have been developed in the form of a compact bush, making them easier to grow in smaller spaces. On healthy pumpkin plants, there is a canopy of large, reniform and serrated leaves, which may be without lobes or with very deep ones. Fruit flesh can be of various shades of yellow, or even from white to orange. The fruits may have a soft or a hard shell with usually orange, but possibly other, colors and various patterns. Pumpkins show a great variety of sizes from small to large and colors from uniform to variegated. The flesh can range from white to yellow and, contrary to the winter squash that has a finely textured flesh, usually has a coarse or stringy flesh. In the United States, the principal pumpkin growing regions are California, Michigan, Ohio, Illinois, Pennsylvania, New York, and Texas which produce approximately 44,000 acres out of a total annual acreage of more than 74,000 acres (USDA, 2000; ERS 1997), but pumpkins are grown in at least a small scale in most States and Canada. Pumpkins are available in the United States in the fall during September and October in association with the Halloween holiday at the end of October. Pumpkins are edible but are usually used for ornamental purposes. The most common food use is in pumpkin pies, but use is limited to a few varieties as winter squash types have more acceptable flesh quality.

*Cucurbita pepo* is a member of the family Cucurbitaceae. The Cucurbitaceae is a family of about 90 genera and 700 to 760 species, mostly of the tropics. The family includes pumpkins, squash, gourds, watermelon, loofah and several weeds. The genus *Cucurbita*, to which the pumpkin belongs, includes four major species, *pepo, argyrosperma, moschata*, and *maxima*, one minor species, *ficifolia* and additional wild species. Cross-pollination is near complete among the different *Cucurbita* species. This offers breeders a great potential for inter-specific crosses using conventional breeding procedures. *Cucurbita pepo* L. refers to what is commonly known as the summer squash such as scallop, zucchini, straightneck and crookneck types and winter squash such as acorn and pumpkin. The term pumpkin itself has a rather broad meaning. Generally, it can be said that if the plant produces fruits to be harvested in a mature stage and are used for pies, jack-o'-lanterns, or stock feed, they are called pumpkins in the U.S.

*Cucurbita pepo* is a simple diploid species with twelve pairs of highly differentiated chromosomes. The plants are monoecious, with separate female and male flowers on the same plant. Usually the first few flowers produced are male, followed by interspersed male and female flowers. Male flowers have 3–5 erect stamens bunched within the corolla of 5 fused petals. Female flowers have 3 spreading stigma lobes and an immature fruit (ovary) below the perianth. The spiny, sticky pollen requires insects for pollination. The primary pollinators are bees, particularly honey bees. Pollination generally occurs in the morning after the flowers open.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

The complexity of inheritance influences choice of the breeding method. Backcross breeding is used to transfer one or a few favorable genes for a heritable trait into a desirable cultivar. This approach has been used extensively for breeding disease-resistant cultivars, nevertheless, it is also suitable for the adjustment and selection of morphological characters, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s) for three or more years. The best lines are candidates for use as parents in new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a focus on clear objectives.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar.

If a single observation is inconclusive, replicated observations provide a better estimate of its genetic worth.

The goal of pumpkin breeding is to develop new, unique and superior pumpkin inbred lines and hybrids. The breeder initially selects and crosses two or more parental lines, followed by repeated self pollination or selfing and selection, producing many new genetic combinations. The breeder can theoretically generate billions of different genetic combinations via crossing, selfing and mutations.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. This unpredictability results in the large expenditure of research funds to develop a superior new pumpkin inbred line.

The development of commercial pumpkin hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable cultivars or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly, crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., "Principles of Plant Breeding" John Wiley and Son, pp. 115–161, 1960; Allard, 1960; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny.

Pumpkin is an important and valuable vegetable crop. Thus, a continuing goal of plant breeders is to develop stable, high yielding pumpkin hybrids that are agronomically and commercially sound. The reasons for this goal are to maximize the amount of fruits produced on the land used (yield) as well as to improve the fruit agronomic qualities. To accomplish this goal, the pumpkin breeder must select and develop pumpkin plants that have the traits that result in superior parental lines that combine to produce superior commercial hybrids.

SUMMARY OF THE INVENTION

According to the invention, there is provided a novel inbred pumpkin line designated ZYPMB24. This invention thus relates to the seeds of inbred pumpkin line ZYPMB24, to the plants or parts thereof of inbred pumpkin line ZYPMB24, to plants or parts thereof having all the physiological and morphological characteristics of inbred pumpkin line ZYPMB24 and to plants or parts thereof having all the physiological and morphological characteristics of inbred pumpkin line ZYPMB24 listed in Table 1 as determined at the 5% significance level when grown in the same environmental conditions. Parts of the inbred pumpkin plant of the present invention are also provided, such as e.g., pollen obtained from an inbred plant and an ovule of the inbred plant.

In another aspect, the present invention provides regenerable cells for use in tissue culture of inbred pumpkin plant ZYPMB24. The tissue culture will preferably be capable of regenerating plants having all the physiological and morphological characteristics of the foregoing inbred pumpkin plant. Preferably, the cells of such tissue cultures will be embryos, meristematic cells, seeds, callus, pollen, ovules, leaves, anthers, roots, root tips, stems, petioles, fruits, cotyledons, hypocotyls, flowers or the like. Protoplasts produced from such tissue culture are also included in the present invention. The pumpkin plants regenerated from the tissue cultures are also part of the invention.

Also included in this invention are methods for producing a pumpkin plant produced by crossing the inbred line ZYPMB24 with itself or another pumpkin line. When crossed with itself, i.e. crossed with another inbred line ZYPMB24 plant or self pollinated, the inbred line ZYPMB24 will be conserved. When crossed with another, different pumpkin line, an F1 hybrid seed is produced. F1 hybrid seeds and plants produced by growing said hybrid seeds are included in the present invention. A method for producing a F1 hybrid pumpkin seed comprising crossing inbred line ZYPMB24 pumpkin plant with a different pumpkin plant and harvesting the resultant hybrid pumpkin seed are also part of the invention. The hybrid pumpkin seed produced by the method comprising crossing inbred line ZYPMB24 pumpkin plant with a different pumpkin plant and harvesting the resultant hybrid pumpkin seed are included in the invention, as are included the hybrid pumpkin plant or parts thereof, seeds included, produced by growing said hybrid pumpkin seed.

In another embodiment, this invention relates to a method for producing the inbred line ZYPMB24 from a collection of seeds, collection containing both inbred line ZYPMB24 seeds and hybrid seeds having ZYPMB24 as a parental line. Such a collection of seed might be a commercial bag of seeds. Said method comprises planting the collection of seeds. When planted, the collection of seeds will produce inbred line ZYPMB24 plants from inbred line ZYPMB24 seeds and hybrid plant from hybrid seeds. The plants having all the physiological and morphological characteristics of pumpkin inbred line ZYPMB24 or possibly having a decreased vigor compared to the other plants grown from the collection of seeds are identified as inbred line ZYPMB24 parent plants. Said decreased vigor is due to the inbreeding depression effect and can be identified for example by a less vigorous appearance for vegetative and/or reproductive characteristics including shorter plant height, small fruits or other characteristics. In pumpkins, the inbred line ZYPMB24 might also be identified from the hybrid plant having ZYPMB24 as a parental line by various genetic traits such as plant habit, fruit size, fruit color, and presence of hard shell. As previously mentioned, if the inbred line ZYPMB24 is self pollinated, the inbred line ZYPMB24 will be preserved, therefore, the next step is controlling pollination of the inbred parent plants in a manner which preserves the homozygosity of said inbred line ZYPMB24 parent plant, the final step being to harvest the resultant seed.

This invention also relates to methods for producing other inbred pumpkin lines derived from inbred pumpkin line ZYPMB24 and to the inbred pumpkin lines derived by the use of those methods.

In another aspect, the present invention provides transformed ZYPMB24 inbred pumpkin line or parts thereof that have been transformed so that its genetic material contains one or more transgenes, preferably operably linked to one or more regulatory elements. Also, the invention provides methods for producing a pumpkin plant containing in its genetic material one or more transgenes, preferably operably linked to one or more regulatory elements, by crossing transformed ZYPMB24 inbred pumpkin line with either a second plant of another pumpkin line, or a non transformed pumpkin plant of the inbred line ZYPMB24, so that the genetic material of the progeny that results from the cross contains the transgene(s), preferably operably linked to one or more regulatory elements. Transgenic pumpkin plants, or parts thereof produced by the method are in the scope of the present invention.

More specifically, the invention comprises methods for producing male sterile pumpkin plants, herbicide resistant pumpkin plants, insect resistant pumpkin plants, disease resistant pumpkin plants, plants with increased sweetness and flavor, plants with increased sugar content, plants with delayed senescence or controlled ripening or plants with improved salt and drought tolerance. Said methods comprise transforming the inbred line ZYPMB24 pumpkin plant with nucleic acid molecules that confer male sterility, herbicide resistance, insect resistance, disease resistance, increased sugar content, delayed senescence or controlled ripening, improved salt tolerance, improved drought tolerance respectively. The transformed pumpkin plants obtained from the provided methods, including male sterile pumpkin plants, herbicide resistant pumpkin plants, insect resistant pumpkin plants, disease resistant pumpkin plants, pumpkin plants with increased sweetness and flavor, pumpkin plants with increased sugar content, pumpkin plants with delayed senescence or controlled ripening, pumpkin plants with improved salt tolerance, pumpkin plants with improved drought tolerance, are included in the present invention. For the present invention and the skilled artisan, disease is understood to be fungal disease, viral disease, bacterial disease or other plant pathogenic diseases and disease resistant plant will encompass plants resistant to fungal, viral, bacterial and other plant pathogens.

In another aspect, the present invention provides for methods of introducing one or more desired trait(s) into the pumpkin line ZYPMB24 and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance for bacterial, fungal, or viral disease, male fertility, enhanced nutritional quality such as increased sugar content or increased sweetness, or enhanced plant quality such as improved drought or salt tolerance and industrial usage. The gene or genes may be naturally occurring pumpkin gene(s) or transgene(s) introduced through genetic engineering techniques. The method for introducing the desired trait(s) is preferably a backcrossing process making use of a series of backcrosses to the inbred pumpkin line ZYPMB24 during which the desired trait(s) is maintained by selection.

When using a transgene, the trait is generally not incorporated into each newly developed line such as ZYPMB24 by direct transformation. Rather, the more typical method used by breeders of ordinary skill in the art to incorporate the transgene is to take a line already carrying the transgene and to use such line as a donor line to transfer the transgene into the newly developed line. The same would apply for a naturally occurring trait The backcross breeding process comprises the following steps: (a) crossing the inbred line ZYPMB24 plants with plants of another line that comprise the desired trait(s), (b) selecting the F1 progeny plants that have the desired trait(s); (c) crossing the selected F1 progeny plants with the inbred line ZYPMB24 plants to produce backcross progeny plants; (d) selecting for backcross progeny plants that have the desired trait(s) and physiological and morphological characteristics of pumpkin inbred line ZYPMB24 to produce selected backcross progeny plants; and (e) repeating steps (c) and (d) one, two, three, four, five six, seven, eight or more times in succession to produce selected, second, third, fourth, fifth, sixth, seventh, eighth or higher backcross progeny plants that comprise the desired trait(s) and the physiological and morphological characteristics of pumpkin inbred line ZYPMB24 as determined in Table 1 at a 5% significance level when grown in the same environmental conditions. The pumpkin plants produced by the methods are also part of the invention. Backcrossing breeding methods, well know for a man skilled in the art of plant breeding will be further developed in subsequent parts of the specification.

In a preferred embodiment, the present invention provides methods for increasing and producing inbred line ZYPMB24 seed, whether by crossing a first inbred parent pumpkin plant with a second inbred parent pumpkin plant and harvesting the resultant pumpkin seed, wherein both said first and second inbred pumpkin plant are the inbred line ZYPMB24, or by planting an inbred pumpkin seed of the inbred pumpkin line ZYPMB24, growing an inbred line ZYPMB24 plant from said seed, controlling a self pollination of the plant where the pollen produced by the grown inbred line ZYPMB24 plant pollinates the ovules produced by the very same inbred line ZYPMB24 grown plant and harvesting the resultant seed.

The invention further provides methods for developing pumpkin plants in a pumpkin plant breeding program using plant breeding technique including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection and transformation. Seeds, pumpkin plants, and parts thereof produced by such breeding methods are also part of the invention.

DEFINITIONS

In the description and tables that follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Relative Fruit Size. As used herein, Relative Fruit Size means the average fruit size per plot within a Fruit Size category (S=small; L=large) and expressed within a group as 1=small; 3=medium; 5=large.

Backcrossing. Backcrossing is a process in which a breeder repeatedly crosses hybrid progeny back to one of the parents, for example, a first generation hybrid $F_1$ with one of the parental genotype of the $F_1$ hybrid.

Cavity. As used herein, cavity refers to the center of the pumpkin fruit containing seeds and maternal tissues.

Essentially all the physiological and morphological characteristics. A plant having essentially all the physiological and morphological characteristics means a plant having the physiological and morphological characteristics, except for the characteristics derived from the converted gene.

Handle Size. Formally called the peduncle (fruit stalk), it is also known as the fruit stem. Handle Size can range from 1=very small to 5 very large. The Handle size is an important marketing feature of a pumpkin.

Firm fruit exterior. Fruit Firmness subjectively tested under field conditions for resistance of fruit exterior against a given pressure. Range is soft, medium, firm and very firm and hard shell.

Fruit Shape. Fruit shape means the conformation of the fruit and generally runs from very flat (height to width ratio less then 0.5) to very tall (height to width ration greater then 1.15).

Season maturity. Maturity is considered the date of the onset of harvest and is Very Early, Early, Mid Early, Main and Late.

Flesh color. Flesh color defined as degree of intensity of orange. Range is pale, medium, medium dark, and deep.

Fruit Color. Fruit color is judged at physiological maturity. Fruit Color ranges from 1=very pale orange to 5=very dark orange.

Quantitative Trait Loci (QTL) Quantitative trait loci refer to genetic loci that control to some degree numerically representable traits that are usually continuously distributed.

Regeneration. Regeneration refers to the development of a plant from tissue culture.

Ribbing. Ribbing means the longitudinal suture or crease in the exterior shell of the pumpkin fruit. Ribbing can range from 1=no ribbing to 5=very deep ribs.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Fruit size. In pumpkin there is a continuous range of size (weight) from less than one pound for the smallest to 60 or more for the largest. Fruits of a related species, *Cucurbita maxima*, also called pumpkin, can be as large as 1200 pounds. In general, Mini pumpkins weigh up to 2 lbs, Small, 3 to 5 lbs, Medium 10 to 20 lbs, Large, 25 lbs. Very large and Giant are above 25 lbs.

Overall Rating. A final or Overall Rating is assigned to variety performance in test or trial situations of a variety. Overall Rating can range from 1=very poor to 5 excellent.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International Convention for the Protection of New Varieties of Plants).

Collection of seeds. In the context of the present invention a collection of seeds will be a grouping of seeds mainly containing similar kind of seeds, for example hybrid seeds having the inbred line of the invention as a parental line, but that may also contain, mixed together with this first kind of seed, a second, different kind of seed, of one of the inbred parent lines, for example the inbred line of the present invention. A commercial bag of hybrid seeds having the inbred line of the invention as a parental line and containing also the inbred line seeds of the invention would be, for example such a collection of seeds.

Decreased vigor: A plant having a decreased vigor in the present invention is a plant that, compared to other plants has a less vigorous appearance for vegetative and/or reproductive characteristics including smaller plant size, smaller fruit, different fruit or leaf shape or other characteristics.

Inbreeding depression: The inbreeding depression is the loss of performance of the inbreds due to the effect of inbreeding, i.e. due to the mating of relatives or to self pollination. It increases the homozygous recessive alleles leading to plants which are weaker and smaller and having other less desirable traits.

Plant Part: As used herein, the term "plant part" includes leaves, stems, roots, seed, embryo, pollen, ovules, flowers, root tips, anthers, tissue, cells and the like.

Plant Cell: Plant cell, as used herein includes plant cells whether isolated in tissue culture or incorporated in a plant or plant part.

DETAILED DESCRIPTION OF THE INVENTION

Inbred pumpkin line ZYPMB24 is a Halloween pumpkin with superior characteristics, and provides an excellent parental line in crosses for producing first generation ($F_1$) hybrid pumpkin. Inbred pumpkin line ZYPMB24 is best adapted to the main areas of cultivation and suitable to all areas of the US where pumpkins are grown. Inbred pumpkin ZYPMB24 produces small fruit with a smooth, slightly ribbed, very deep orange-colored shell and with thick firm flesh of a yellow orange color. It has a heavy, dark colored, strong stem. It has a desirable uniformly flat round shape, the height averaging slightly less than the width. It grows on a trailing vine. It is resistant to powdery mildew. Inbred ZYPM24B can be used to produce main season maturity hybrid pumpkin varieties having good yield, with small to medium fruit, good fruit color, large peduncle (fruit stalks or stem), and resistant to powdery mildew.

Inbred pumpkin line ZYMPB24 has superior characteristics and was developed from the F1 cross between pumpkin inbred B25C, which is a powdery mildew resistant line, and pumpkin inbred ZYB24A, a line resistant to Zucchini Yellow Mosaic Virus. This cross was made in 1996 in the field at Harris Moran Research Station in Davis, Calif. The $F_2$ population was grown in Jupiter, Fla. (plot 2070) in the spring of 1998, with selections for the combination of both PM and ZYMV resistances. $F_3$ populations were grown in Davis, Calif. in the summer of 1998, (plots 4873 and 4874) and again selections were made for the same disease resistances. The $F_4$ populations were grown in summer, 1999 (plots 4333 and 4334) in Davis, Calif. In 2000 seed from a selection from 1999 plot 4334 was used in a cage foundation seed increase.

Inbred ZYPMB24 is similar to the standard open pollinated cultivar 'Small Sugar', but does have significant differences. 'Small Sugar' is a vine, while ZYPMB24 is bushy. 'Small Sugar' is susceptible to powdery mildew and Zucchini Yellow Mosaic Virus, while ZYPMB24 is resistant to both diseases. The mature fruits of 'Small Sugar' are orange, deeply ribbed, and have medium size peduncles, while ZYPMB24 fruits are dark orange, shallowly ribbed, and have large peduncles.

During the development of the line, crosses were made to inbred testers for the purpose of estimating the line's general and specific combining ability, and parallel evaluations were run in the USA at the Davis, Calif. Research Station. The inbred was evaluated further as a line and in numerous crosses at the Davis, Calif. Research station. The inbred has proven to have a good combining ability in hybrid combinations.

The inbred line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred ZYPMB24.

Inbred pumpkin line ZYPMB24 has the following morphologic and other characteristics (based primarily on data collected at Davis, Calif.).

TABLE 1

VARIETY DESCRIPTION INFORMATION

Plant Type: Pumpkin
Genus: *Cucurbita*
Species: *pepo*
Region where developed: Florida and California
Area of best adaptation in the USA: All U.S.
Plant: Semi-bush
Prickly
Main Stem: Angled
Average length (cm): 216
Diameter at midpoint of first internode (mm): 23
Average number of internodes: 46
Leaves:
Shape: Reniform; shallow lobed
Margin: Dentate, frilled
Width (cm): 28
Length (cm): 32
Surface: smooth
Dorsal surface: soft hairy
Ventral surface: bristled
Color: Medium green, not blotched
Petiole length (cm): 34
Flower - Pistillate
Diameter (cm): 18
Ovary: Drum-like
Pedicel length (cm): 3.5
Margin: curved, plain
Sepals width (mm): 1 Length (mm): 11
Color: Lemon yellow center, deep yellow-orange outer
Flower - staminate:
Sepals: width (mm): 2 Length (mm): 24
Pedicel length (cm): 28
Color: Lemon yellow center, deep yellow-orange outer
Fruit:
Length (cm): 12
Width (cm) stem end: 14
Width (cm) blossom end: 14
Average weight (gm): 1,115
Shape according to variety type: Connecticut Field
Apex: flattened
Base: depressed
Ribs: prominent
Rib furrows: Shallow, medium wide
Fruit surface: smooth
Warts: none
Blossom scar button: depressed
Rind:
Thickness at medial (mm): 1
Rind: hard
Color pattern: regular, orange
Flesh:
Thickness: Blossom end (mm): 11
Medial (mm): 116
Stem end (mm): 14
Texture: stringy, firm, moist
Flavor: slightly sweet
Quality: good
Color: yellow orange
Seed Cavity (sectioned apex to base)
Length (cm): 9
Width (cm): 11
Location: conforms to fruit shape
Placental Tissue: abundant
Center core: inconspicuous
Fruit Stalks: slightly curved, irregular, not twisted, tapered
Length (cm): 12
Diameter (cm): 2.5
Texture: hard
Furrows: deep

TABLE 1-continued

VARIETY DESCRIPTION INFORMATION

Surface: spiny
Attachment end: expanded
Detaches: with difficulty
Color: dark green
Seeds
Length (mm): 16
Width (mm): 10
Thickness (mm): 2.4
Face Surface: Smooth
Color: Cream
Luster: Dull
Margin: rounded
Separation from pulp: moderately easy
Grams per 100 seeds: 12
No. seeds per fruit: 282
Yield: 1–3 fruit per plant

FURTHER EMBODIMENTS OF THE INVENTION

This invention is also directed to methods for producing a pumpkin plant by crossing a first parent pumpkin plant with a second parent pumpkin plant wherein either the first or second parent pumpkin plant is an inbred pumpkin plant of the line ZYPMB24. Further, both first and second parent pumpkin plants can come from the inbred pumpkin line ZYPMB24. When self-pollinated, or crossed with another inbred line ZYPMB24 plant, the inbred line ZYPMB24 will be stable while when crossed with another, different pumpkin line, an F1 hybrid seed is produced.

An inbred line is produced through several cycles of self-pollination and is therefore considered a homozygous line.

A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting F1 hybrid, theoretically in the arrangement and organization created by the plant breeder in the original parental line.

As long as the homozygosity of the parental lines is maintained, the resulting hybrid cross is stable. The F1 hybrid is then a combination of phenotypic characteristics issued from two arrangements and organizations of genes, both created by one skilled in the art of the plant breeding process.

Still further, this invention also is directed to methods for producing an inbred pumpkin line ZYPMB24-derived pumpkin plant by crossing inbred pumpkin line ZYPMB24 with a second pumpkin plant and growing the progeny seed, and repeating the crossing and growing steps with the inbred pumpkin line ZYPMB24-derived plant from 0 to 7 times. Thus, any such methods using the inbred pumpkin line ZYPMB24 are part of this invention: selfing, backcrosses, hybrid production, crosses to populations, and the like. All plants produced using inbred pumpkin line ZYPMB24 as a parent are within the scope of this invention, including plants derived from inbred pumpkin line ZYPMB24. Advantageously, the inbred pumpkin line is used in crosses with other, different, pumpkin inbreds to produce first generation ($F_1$) pumpkin hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which pumpkin plants can be regenerated, plant calli, plant clumps and plant cells that are intact in plants or parts of plants, such as embryos, meristematic cells, callus, pollen, ovules, flowers, seeds, leaves, roots, root tips, anthers, stems, petioles, fruits, cotyledons and hypocotyls.

As it is well known in the art, tissue culture of *Cucurbita pepo* can be used for the in vitro regeneration of *Cucurbita pepo*. Tissues cultures of various tissues of *Cucurbita pepo* and regeneration of plants therefrom are well known and published. By way of example, a tissue culture comprising organs has been used to produce regenerated plants as described in Chee-PP. Hort Science, 1992, 27:1, 59–60, Chee-PP. Plant Cell Report 1991, 9:11, 620–622, Juretic et al., Plant Cell Report. 1991, 9:11, 623–626, Rakoczy et al., Plant Cell Tissue and Organ Culture 1989, 18:2, 191–194. Jelaska, Planta 103:278–280 (1972) and Acta Bot. Croat. 32: 81–94 (1973) reported somatic embryogenesis in hypocotyl and cotyledon-derived callus of pumpkins and demonstrated that embryos could develop into normal plants. Pink et al., Sci. Hortic. 24:107–114 (1984) reported a rapid propagation method for pumpkin through apical meristem culture. It is clear from the literature that the state of the art is such that these methods of obtaining plants are "conventional" in the sense that they are routinely used and have a very high rate of success. Thus, another aspect of this invention is to provide cells which, upon growth and differentiation, produce pumpkin plants having the physiological and morphological characteristics of inbred pumpkin line ZYPMB24.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed pumpkin plants, using transformation methods as described below to incorporate transgenes into the genetic material of the pumpkin plant(s).

Expression Vectors for Pumpkin Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Valles et al., Plant Cell Report, 13:3–4 145–148 (1994), Fang et al., Plant Cell Report, 9:3 160–164 (1990). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986). Other selectable marker genes confer resistance to herbicides such as glyphosate, glufosinate or broxynil. Comai et al., Nature 317:741–744 (1985), Gordon-Kamm et al., Plant Cell 2:603–618 (1990) and Stalker et al., Science 242:419–423 (1988).

Other selectable marker genes for plant transformation that are not of bacterial origin include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984), Valles et al, Plant Cell Report 3:3–4 145–148 (1994), Shetty et al., FoodBiotechnology 11:2 111–128 (1997)

In vivo methods for visualizing GUS activity that do not require destruction of plant tissue are also available. However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters—Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain organs, such as leaves, roots, seeds and tissues such as fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in pumpkin. Optionally, the inducible promoter is operably linked to a nucleotide sequence encoding a signal sequence which is operably linked to a gene for expression in pumpkin. With an inducible promoter the rate of transcription increases in response to an inducing agent.

Any inducible promoter can be used in the instant invention. See Ward et al., Plant Mol. Biol. 22:361–366 (1993). Exemplary inducible promoters include, but are not limited to, that from the ACEI system which responds to copper (Mett et al., PNAS 90:4567–4571 (1993)); In2 gene from maize which responds to benzenesulfonamide herbicide safeners Gatz et al., Mol. Gen. Genetics 243:32–38 (1994) or Tet repressor from Tn10 Gatz et al., Mol. Gen. Genetics 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter is operably linked to a gene for expression in pumpkin or the constitutive promoter is operably linked to a nucleotide sequence encoding a signal sequence which is operably linked to a gene for expression in pumpkin.

Many different constitutive promoters can be utilized in the instant invention. Exemplary constitutive promoters include, but are not limited to, the promoters from plant viruses such as the 35S promoter from CaMV (Odell et al., Nature 313:810–812 (1985)) and the promoters from such genes as rice actin (McElroy et al., Plant Cell 2:163–171 (1990)); ubiquitin (Christensen et al., Plant Mol. Biol.

12:619–632 (1989) and Christensen et al., Plant Mol. Biol. 18:675–689 (1992)); pEMU (Last et al., Theor. Appl. Genet. 81:581–588 (1991)); MAS (Velten et al., EMBO J. 3:2723–2730 (1984)) and maize H3 histone (Lepetit et al., Mol. Gen. Genetics 231:276–285 (1992) and Atanassova et al., Plant Journal 2 (3): 291–300 (1992)).

The ALS promoter, XbZYPMB24/NcoI fragment 5' to the *Brassica napus* ALS3 structural gene (or a nucleotide sequence similarity to said XbZYPMB24/NcoI fragment), represents a particularly useful constitutive promoter. See PCT application WO96/30530.

C. Tissue-specific or Tissue-preferred Promoters

A tissue-specific promoter is operably linked to a gene for expression in pumpkin. Optionally, the tissue-specific promoter is operably linked to a nucleotide sequence encoding a signal sequence which is operably linked to a gene for expression in pumpkin. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476–482 (1983) and Sengupta-Gopalan et al., Proc. Natl. Acad. Sci. U.S.A. 82:3320–3324 (1985)); a leaf-specific and light-induced promoter such as that from cab or rubisco (Simpson et al., EMBO J. 4(11):2723–2729 (1985) and Timko et al., Nature 318:579–582 (1985)); an anther-specific promoter such as that from LAT52 (Twell et al., Mol. Gen. Genetics 217: 240–245 (1989)); a pollen-specific promoter such as that from Zm13 or a microspore-preferred promoter such as that from apg (Twell et al., Sex. Plant Reprod. 6:217–224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Knox, C., et al., Plant Mol. Biol. 9:3–17 (1987), Lerner et al., Plant Physiol. 91:124–129 (1989), Fontes et al., Plant Cell 3:483–496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., Cell 39:499–509 (1984), Stiefel, et al., Plant Cell 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92–6 (1981).

According to a preferred embodiment, the transgenic plant provided for commercial production of foreign protein is pumpkin. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt-$\alpha$-endotoxin gene. Moreover, DNA molecules encoding $\alpha$-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor 1), Sumitani et al., Biosci. Biotech. Biochem. 57:1243 (1993) (nucleotide sequence of *Streptomyces nitrosporeus* α-amylase inhibitor).

F. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper-accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance).

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect.

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-endo-α-1,4-D-galacturonase. See Lamb et al., BioTechnology 10:1436 (1992). The cloning and characterization of a gene which encodes a bean endopolygalacturonase-inhibiting protein is described by Toubart et al., Plant J. 2:367 (1992).

R. A developmental-arrestive protein produced in nature by a plant. For example, Logemann et al., BioTechnology 10:305 (1992), have shown that transgenic plants expressing the barley ribosome-inactivating gene have an increased resistance to fungal disease.

S. A combination of Zucchini Yellow Mosaic Potyvirus and Watermelon Mosaic 2 Potyvirus coat proteins expressed by transgenic *Cucurbita* lines and preventing such lines from developing severe foliar symptoms. See Fuchs et al., BioTechnology. 1995,13:13, 1466–1473.

2. Genes That Confer Resistance to an Herbicide, For Example:

A. An herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., BioTechnology 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2 and Acc1-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes That Confer or Contribute to a Value-Added Trait, Such as:

A. Increased sweetness and flavor of the fruit by introduction of a gene encoding sweet tasting proteins such as monellin, see for example Penarrubia et al., Biotechnology. 1992, 10:5, 561–564 or thaumatin, see Bartoszewski et al, Plant Breeding 122, 347–351 (2003).

B. Reduced ethylene biosynthesis to control ripening by introduction of an antisense construct of ACC oxidase. For example, see Ayub et al, Nature Biotechnology 14:862 (1996).

C. Delayed senescence and improved ripening control by transferring a gene or acting on the transcription of a gene involved in plant senescence. See Wang et al. In Plant Mol. Bio. 52:1223–1235 (2003) on the role of the deoxyhypusine synthase in senescence. See also U.S. Pat. No. 6,538,182 issued Mar. 25$^{th}$, 2003.

D. Improved salt tolerance by transforming plants with HAL 1, a yeast regulatory gene involved in stress tolerance, as shown in Serrano et al., Scientia Horticuturae. 1999, 78: 1/4, 261–269 or in Bordas et al., Transgenic Research. 1997, 6: 1,41–50.

E. Obtained male sterile plants, especially useful in hybrid melon production, by introduction of a gene encoding a tobacco PR Glucanase as described in tomato (WO9738116) but that can also be used in pumpkins.

Methods for Pumpkin Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89–119.

A. *Agrobacterium*-mediated Transformation

One method for introducing an expression vector into plants is based on the natural transformation system of *Agrobacterium*. See, for example, Horsch et al., Science 227:1229 (1985), Jefferson et al., Embo J. 3901–390764, (1987), Valles et al., PI Cell. Rep. 145–148:13 (1984). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., The Plant Journal 6:271–282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., BioTechnology 6:559–563 (1988), Sanford, J. C., Physiol Plant 7:206 (1990), Klein et al., Biotechnology 10:268 (1992). Gonzalves et al., Journal of the American Society for Horticultural Science. 1994, 119: 2, 345–355, Gray et al., Plant Cell Tissue and Organ Culture. 1994, 37:2, 179–184.

Another method for physical delivery of DNA to plants is sonication of target cells. Zhang et al., BioTechnology 9:996 (1991). Alternatively, liposome or spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described. D'Halluin et al., Plant Cell 4:1495–1505 (1992) and Spencer et al., Plant Mol. Biol. 24:51–61 (1994).

Following transformation of pumpkin target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular pumpkin line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred pumpkin plant is used in the context of the present invention, this also includes any inbred pumpkin plant where one or more desired trait has been introduced through backcrossing methods, whether such trait is a naturally occurring one or a transgenic one. Backcrossing methods can be used with the present invention to improve or introduce one or more characteristic into the inbred. The term backcrossing as used herein refers to the repeated crossing of a hybrid progeny back to one of the parental pumpkin plants for that inbred. The parental pumpkin plant which contributes the gene or the genes for the desired characteristic is termed the nonrecurrent or donor parent. This terminology refers to the fact that the nonrecurrent parent is used one time in the backcross protocol and therefore does not recur. The parental pumpkin plant to which the gene or genes from the nonrecurrent parent are transferred is known as the recurrent parent as it is used for several rounds in the backcrossing protocol (Fehr, 1987).

In a typical backcross protocol, the original inbred of interest (recurrent parent) is crossed to a second inbred (nonrecurrent parent) that carries the gene or genes of interest to be transferred. The resulting progeny from this cross are then crossed again to the recurrent parent and the process is repeated until a pumpkin plant is obtained wherein all the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self pollination and growing of population might be included between two successive backcrosses. Indeed, an appropriate selection in the population produced by the self pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self pollinated to produce a population of plants where selection is practiced for the plants having the desired trait of parent B and physiological and morphological characteristics of parent A, d) the selected plants are backcrossed one, two, three, four, fifth or more times to parent A to produce selected backcross progeny plants comprising the desired trait of parent B and physiological and morphological characteristics of parent A. Step c) may or may not be repeated and included between the backcrosses of step d.

The selection of a suitable recurrent parent is an important step for a successful backcrossing procedure. The goal of a backcross protocol is to alter or substitute one or more trait(s) or characteristic(s) in the original inbred. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important that the identification of the character(s) in the segregating population. In this instance it may then be necessary to introduce a test of the progeny to determine if the desired characteristic(s) has been successfully transferred. Such tests encompass visual inspection, simple crossing but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the naked seed coat in pumpkin require selfing the progeny to determine which plant carries the recessive allele(s).

Many single gene traits have been identified that are not regularly selected for in the development of a new inbred but that can be improved by backcrossing techniques. Single gene traits may or may not be transgenic, i.e. they may be naturally present in the non recurrent parent. Examples of these traits include but are not limited to, male sterility, herbicide resistance (such as pat or bar genes), resistance for bacterial, fungal or viral disease (capsid protein genes, insect resistance), male fertility, enhanced nutritional quality, enhanced sugar content, yield stability and yield enhancement, and resistance to ZYMV in pumpkin. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

In 1981 the backcross method of breeding accounted for 17% of the total breeding effort for inbred line development in the United States, according to, Hallauer, A. R. et al. (1988) "Corn Breeding" Corn and Corn Improvement, No. 18, pp. 463–481.

The backcross breeding method provides a precise way of improving varieties that excel in a large number of attributes but are deficient in a few characteristics. (Page 150 of the Pr. R. W. Allard's 1960 book, published by John Wiley & Sons, Inc, "Principles of Plant Breeding). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a variety with exactly the adaptation, yielding ability and quality characteristics of the recurrent parent but superior to that parent in the particular characteristic(s) for which the improvement program was undertaken. Therefore, this method provides the plant breeder with a high degree of genetic control of his work.

The method is scientifically exact because the morphological and agricultural features of the improved variety could be described in advance and because the same variety could, if it were desired, be bred a second time by retracing the same steps (Briggs, "Breeding wheats resistant to bunt by the backcross method", 1930 Jour. Amer. Soc. Agron., 22: 289–244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Successful backcrosses are for example the transfer of stem rust resistance from "Hope" wheat to "Bart wheat" and even pursuing the backcrosses with the transfer of bunt resistance to create "Bart 38", having both resistances. Also highlighted by Allard is the successful transfer of mildew, leaf spot and wilt resistances in California Common alfalfa to create Caliverde. This new Caliverde variety produced through the backcross process is indistinguishable from California Common except for its resistance to the three named diseases.

One of the advantages of the backcross method is that the breeding program can be carried out in almost every environment that will allow the development of the character being transferred.

The backcross technique is not only desirable when breeding for disease resistance but also for the adjustment of morphological characters, colour characteristics and simply inherited quantitative characters such as earliness, plant height and seed size and shape. In this regard, a medium grain type variety, Calady, has been produced by Jones and Davis. In dealing with quantitative characteristics, the donor parent was selected with the view of sacrificing some of the intensity of the character for which it was chosen, i.e. grain size. Lady Wright, a long grain variety was used as the donor parent and Coloro, a short grain one as the recurrent parent. After four backcrosses, the medium grain type variety Calady was produced.

Tables

In the tables that follow, the traits and characteristics of hybrid combinations having inbred pumpkin ZYPMB24 as a parental line are given compared to other hybrids. The data collected are presented for key characteristics and traits. The field tests have been made at numerous locations, with two or three replications per location. Information about these hybrids, as compared to the check hybrid is presented.

Data are subjective ratings of 1 to 5, where fruit size: 1=small, 5=large; fruit shape: 1=very flat, 3=round, 5=very tall; fruit color: 1=very pale, 5=very dark; ribbing: 1=no ribbing, 5=very deep ribs; handle size: 1=very small, 5=very large and overall rating: 1=very poor, 5=excellent.

TABLE 2

Data from Davis, CA, summer, 2004

| Hybrid Combination | Relative Fruit Size | Fruit Shape | Fruit Color | Ribbing | Handle Size | Overall Rating |
|---|---|---|---|---|---|---|
| Rep. 1 | | | | | | |
| Magic Lantern | L3 | 3 | 4 | 3 | 3 | 4 |
| ZYPMB24 × ZYD5B | L2 | 3 | 3 | 3 | 3 | 3 |
| ZYPMB24 × P102 | L3 | 3 | 3.5 | 3 | 4.5 | 4 |
| ZYPMB24 × B48B | S3 | 3 | 3.5 | 2 | 3 | 4 |
| ZYPMB24 × G31 | S2.5 | 3 | 4 | 1.5 | 4 | 4 |
| ZYPMB24 × G32 | S2.9 | 2.5 | 4 | 1 | 3 | 2 |
| ZYPMB24 × G17B25C | S2.5 | 3 | 4.5 | 2 | 4 | 4 |
| ZYPMB24 × B33B | S3.5 | 3 | 4 | 2 | 3 | 4 |
| Rep. 2 | | | | | | |
| Magic Lantern | L2 | 3 | 3 | 3 | 3 | 3 |
| ZYPMB24 × ZYD5B | L2.5 | 3 | 3 | 4 | 3.5 | 4 |
| ZYPMB24 × P102 | L2.5 | 3 | 3.5 | 3 | 4 | 4 |
| ZYPMB24 × B48B | S3 | 2.5 | 3 | 1.5 | 3 | |
| ZYPMB24 × G31 | S2.5 | 2.5 | 3.5 | 1 | 3.5 | 4 |
| ZYPMB24 × G32 | S3 | 2.5 | 3.5 | 1 | 3 | 4 |
| ZYMPB24 × G17B25C | S2.5 | 3 | 4 | 1.5 | 4 | 4 |

TABLE 3

Data from Benton Harbor, MI, summer, 2004

| Hybrid Combination | Relative Fruit Size | Fruit Shape | Fruit Color | Ribbing | Handle Size | Overall Rating |
|---|---|---|---|---|---|---|
| Magic Lantern | L4 | 3 | 4.5 | 4 | 3 | |
| ZYD5B × ZYPMB24 | L3.5 | 3 | 3.5 | 3.5 | 4 | |
| ZYPMB24 × P102 | L4 | 2 | 3 | 2 | 4.5 | 4 |
| ZYPMB24 × B48B | L1.5 | 3 | 3 | 1.5 | 3 | |
| ZYPMB24 × G31 | L1.3 | 2.5 | 3.5 | 1.5 | 3 | 4 |

TABLE 4

Data from Amos Martin Farm, PA, summer, 2004

| Hybrid Combination | Relative Fruit Size | Fruit Shape | Fruit Color | Ribbing | Handle Size | Overall Rating |
|---|---|---|---|---|---|---|
| Magic Lantern | L3 | 3 | 3 | 4 | 3 | 4 |
| ZYPMB24 × P102 | L3.5 | 3 | 3.5 | 3 | 3.5 | 4 |

TABLE 5

Hybrid comparison made at South Charleston, Ohio, in 2003

| Hybrid Combination | Downy Mildew (3) | Virus (3) | Foliar Powdery Mildew Rating (1) | Powdery Mildew on Handle (3) | Anthracnose (2) |
|---|---|---|---|---|---|
| Pro Gold 510 | 1 | 1 | 5.3 | 1 | 8 |
| Gold Gem | 1 | 1 | 5.8 | 1.5 | 8.5 |
| Gold Medal | 1 | 1 | 5.5 | 1.8 | 9 |
| ZYPMB24 × P102 | 1.8 | 1.5 | 3.8 | 1.8 | 7.3 |
| ZYPMB24 × ZYD5B | 1.8 | 1 | 3.8 | 2 | 7.5 |
| ZYPMB24 × D48B | 1.8 | 1.3 | 4.3 | 1.5 | 7.8 |
| LSD 0.05% | | | 0.8 | | 4.8 |

Key to Disease Ratings in Table 1.
1. PM: 1=no or a trace of mildew, 2=1–25%, 3=26–50%, 4=51–75%, 5=76–100% foliage with fungal colonies and 6=necrotic leaves.
2. Anthracnose: 1=no or a trace of mildew, 2=1 to 20%, 3=21 to 30, and so on to 10=all foliage affected and/or dead foliage.
3. Downy Mildew, Powdery Mildew on handle and Virus Rating: 1=presence of downy mildew on foliage; powdery on handle; or virus on foliage; 2=no powdery mildew on handle, downy mildew or virus on foliage

DEPOSIT INFORMATION

Deposits of the Harris Moran Seed Company proprietary inbred pumpkin line ZYPMB24, pumpkin hybrid seed ZYPMB24*ZYD5B, pumpkin hybrid seed YPMB24*P102, pumpkin hybrid seed ZYPMb 24*B48B, pumpkin hybrid seed ZYPMB24*G31, pumpkin hybrid seed ZYPMB24*G32, pumpkin hybrid seed ZYPMB24*G17B25C, and pumpkin hybrid seed ZYPMB24*B33B disclosed above and recited in the appended claims have been made with National Collections of Industrial Food and Marine Bacteria (NCIMB), 23 St. Machar Drive, Aberdeen, Scotland, AB24 3RY, United Kingdom. The date of deposit was Aug. 3, 2006 for inbred pumpkin line ZYPMB24, pumpkin hybrid seed ZYPMB24*PI02, pumpkin hybrid seed ZYPMB24*B48B, pumpkin hybrid seed ZYPMB24*G17B25C and pumpkin hybrid seed ZYPMB24*B33B. The date of deposit was Aug. 7, 2006 for pumpkin hybrid seed ZYPMB24*G31 and pumpkin hybrid seed ZYPMB24*G32. The date of deposit was Jul. 3, 2006 for pumpkin hybrid seed ZYPMB24*ZYD5B. The deposits of 2.500 seeds each were taken from the same deposits maintained by Harris Moran Seed Company since prior to the filing date of this application. All restrictions upon the deposits have been removed, and the deposits are intended to meet all of the requirements of 37 C.F.R. §1.801–1.809. The NCIMB accession number for inbred pumpkin line ZYPMB24 is NCIMB 41420. The NCIMB accession number for pumpkin hybrid seed ZYPMB24*ZYD5B is NCIMB 41411. The NCIMB accession number for pumpkin hybrid seed ZYPMB24*P102 is NCIMB 41423. The NCIMB accession number for pumpkin hybrid seed ZYPMB24*B48B is NCIMB 41424. The NCIMB accession number for pumpkin hybrid seed ZYPMB24*G31 is NCIMB 41425. The NCIMB accession number for pumpkin hybrid seed ZYPMB24*G32 is NCIMB 41426. The NCIMB accession number for pumpkin hybrid seed ZYPMB24*G17B25C is NCIMB 41422. The NCIMB accession number for pumpkin hybrid seed ZYPMB24*B33B is NCIMB 41421. The deposits will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. A seed of inbred pumpkin line designated ZYPMB24, wherein a representative sample of seed of said line was deposited under NCIMB 41420.

2. A pumpkin plant, or a part thereof, produced by growing the seed of claim 1.

3. A pumpkin plant, or a part thereof, having all the physiological and morphological charactoristics of the inbred line ZYPMB24 listed in Table 1.

4. A pumpkin plant, or a part thereof, having the physiological and morphological characteristics of the inbred line ZYPMB24, wherein a representative sample of seeds of said line was deposited under NCIMB 41420.

5. A tissue culture of cells produced from the plant of claim 2.

6. A protoplast produced from the tissue culture of claim 5.

7. The tissue culture according to claim 5, wherein cells of the tissue culture are from a plant part selected from the group consisting of embryos, meristematic cells, callus, pollen, ovules, pistils, flowers, seeds, leaves, roots, root tips, anthers, stems, petioles, fruits, cotyledons and hypocotyls.

8. A pumpkin plant regenerated from the tissue culture of claim 5, wherein the regenerated plant has all of the morphological and physiological characteristics of inbred line ZYPMB24, and wherein a representative sample of seed of said line was deposited under NCIMB 41420.

9. A method for producing a hybrid pumpkin seed wherein the method comprises crossing the plant of claim 2 with a different pumpkin plant and harvesting the resultant hybrid pumpkin seed.

10. A method for producing a male sterile pumpkin plant wherein the method comprises transforming the pumpkin plant of claim 2 with a nucleic acid molecule that confers male sterility.

11. A male sterile pumpkin plant produced by the method of claim 10.

12. A method of producing an herbicide resistant pumpkin plant comprising transforming the pumpkin plant of claim 2 with a transgene that confers herbicide resistance.

13. An herbicide resistant pumpkin plant produced by the method of claim 12.

14. The pumpkin plant of claim 13, wherein the transgene confers resistance to an herbicide selected from the group consisting of imidazolinone, sulfonylurea, glyphosate, glufosinate, L-phosphinothricin, triazine and benzonitrile.

15. A method of producing an insect resistant pumpkin plant wherein the method comprises transforming the pumpkin plant of claim 2 with a transgene that confers insect resistance.

16. An insect resistant pumpkin plant produced by the method of claim 15.

17. The pumpkin plant of claim 16, wherein the transgene encodes a *Bacillus thuringiensis* protein.

18. A method of producing a disease resistant pumpkin plant wherein the method comprises transforming the pumpkin plant of claim 2 with a transgene that confers disease resistance.

19. A disease resistant pumpkin plant produced by the method of claim 18.

20. A method of producing a pumpkin plant with improved ripening control wherein the method comprises transforming the pumpkin plant of claim 2 with a transgene that confers improved ripening control.

21. A pumpkin plant with improved ripening control produced by the method of claim 20.

22. A method of producing a pumpkin plant with improved salt tolerance wherein the method comprises transforming the pumpkin plant of claim 2 with a transgene that confers improved salt tolerance.

23. A pumpkin plant with improved salt tolerance produced by the method of claim 22.

24. A method of introducing a desired trait into inbred pumpkin line ZYPMB24 wherein the method comprises:
  (a) crossing the inbred line ZYPMB24 plants grown from the inbred line ZYPMB24 seed, wherein a representative sample of seed was deposited under NCIMB 41420, with plants of another pumpkin line that comprise a desired trait to produce F1 progeny plants, wherein the desired trait is selected from the group consisting of male sterility, male fertility, herbicide resistance, insect resistance, disease resistance, increased sugar content, increased sweetness, increased flavor, improved ripening control, and improved salt tolerance[, and improved drought tolerance];
  (b) selecting F1 progeny plants that have the desired trait to produce selected F1 progeny plants;
  (c) crossing the selected F1 progeny plants with the inbred line ZYPMB24 plants to produce backcross progeny plants;
  (d) selecting for backcross progeny plants that have the desired trait and physiological and morphological characteristics of inbred pumpkin line ZYPMB24 listed in Table 1 to produce selected backcross progeny plants; and
  (e) repeating steps (c) and (d) three or more times in succession to produce selected fourth or higher backcross progeny plants that comprise the desired trait and all of the physiological and morphological characteristics of inbred pumpkin line ZYPMB24 listed in Table 1.

25. A pumpkin plant produced by the method of claim 24, wherein the plant has the desired trait and the physiological and morphological characteristics of inbred pumpkin line ZYPMB24 listed in Table 1.

26. A method for producing inbred line ZYPMB24 seed, wherein a representative sample of seed was deposited under NCIMB 41420, wherein the method comprises crossing a first inbred parent pumpkin plant with a second inbred parent pumpkin plant and harvesting the resultant pumpkin seed, wherein both said first and second inbred parent pumpkin plant are the pumpkin plants of claim 2.

27. A method for producing inbred line ZYPMB24 seed, wherein a representative sample of seed of which was deposited under NCIMB 41420, wherein the method comprises:
  a) planting an inbred pumpkin seed of claim 1;
  b) growing plant from said seed;
  c) controlling pollination in a manner that the pollen produced by the grown plant pollinates the ovules produced by the grown plant; and
  d) harvesting the resultant seed.

28. A hybrid pumpkin seed designated ZYPMB24*ZYD5B having inbred pumpkin line ZYPMB24 as a parental line, wherein a representative sample of seed of said hybrid was deposited under NCIMB 41411.

29. A hybrid pumpkin plant produced by growing the hybrid pumpkin seed of claim 28.

30. A hybrid pumpkin seed designated ZYPMB24*P102 having inbred pumpkin line ZYPMB24 as a parental line, wherein a representative sample of seed of said hybrid was deposited under NCIMB 41423.

31. A hybrid pumpkin plant produced by growing the hybrid pumpkin seed of claim 30.

32. A hybrid pumpkin seed designated ZYPMB24*B48B having inbred pumpkin line ZYPMB24 as a parental line, wherein a representative sample of seed of said hybrid was deposited under NCIMB 41424.

33. A hybrid pumpkin plant produced by growing the hybrid pumpkin seed of claim 32.

34. A hybrid pumpkin seed designated ZYPMB24*G31 having inbred pumpkin line ZYPMB24 as a parental line, wherein a representative sample of seed of said hybrid was deposited under NCIMB 41425.

35. A hybrid pumpkin plant produced by growing the hybrid pumpkin seed of claim 34.

36. A hybrid pumpkin seed designated ZYPMB24*G32 having inbred pumpkin line ZYPMB24 as a parental line, wherein a representative sample of seed of said hybrid was deposited under NCIMB 41426.

37. A hybrid pumpkin plant produced by growing the hybrid pumpkin seed of claim 36.

38. A hybrid pumpkin seed designated ZYPMB24*G17B25C having inbred pumpkin line ZYPMB24 as a parental line, wherein a representative sample of seed of said hybrid was deposited under NCIMB 41422.

39. A hybrid pumpkin plant produced by growing the hybrid pumpkin seed of claim 38.

40. A hybrid pumpkin seed designated ZYPMB24*B33B having inbred pumpkin line ZYPMB24 as a parental line, wherein a representative sample of seed of said hybrid was deposited under NCIMB 41421.

41. A hybrid pumpkin plant produced by growing the hybrid pumpkin seed of claim 40.

* * * * *